United States Patent [19]

Sayo et al.

[11] Patent Number: 4,981,992

[45] Date of Patent: Jan. 1, 1991

[54] PROCESS FOR PREPARING OPTICALLY ACTIVE 3-HYDROXYBUTANOIC ACID

[75] Inventors: Noboru Sayo; Takao Saito; Yoshiki Okeda; Hiroyuki Nagashima; Hidonori Kumobayashi, all of Kanagawa, Japan

[73] Assignee: Takasago International Corporation, Tokyo, Japan

[21] Appl. No.: 435,877

[22] Filed: Nov. 14, 1989

[30] Foreign Application Priority Data

Nov. 15, 1988 [JP] Japan .................. 63-288032

[51] Int. Cl.$^5$ ............. C07C 67/00; C07C 69/003
[52] U.S. Cl. .................... 560/23; 560/160; 560/170; 562/567; 540/362
[58] Field of Search ............ 560/170, 160, 23

[56] References Cited

U.S. PATENT DOCUMENTS

| 4,194,051 | 3/1980 | Bachman et al. | 560/170 |
| 4,220,590 | 9/1980 | Knowles et al. | 560/23 |
| 4,916,252 | 4/1990 | Sayo et al. | 560/170 |

Primary Examiner—J. E. Evans
Attorney, Agent, or Firm—Sughrue, Mion, Zinn, Macpeak & Seas

[57] ABSTRACT

A process for preparing an optically active 3-hydroxybutanoic acid represented by formula (I):

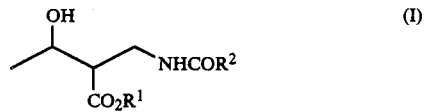

wherein:
$R^1$ represents a protective group of carboxylic acid, and
$R^2$ represents a hydrogen atom; a lower alkyl group which may be substituted with a halogen atom; a lower alkoxy group; a phenyl group which may be substituted with a lower alkyl group or a lower alkoxy group; or a benzyloxy group which may be substituted with a lower alkyl group or a lower alkoxy group, is disclosed, comprising asymmetrically hydrogenating a 3-oxobutanoic acid ester represented by formula (II):

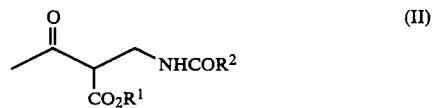

wherein $R^1$ and $R^2$ are as defined above, in the presence of a ruthenium-optically active phosphine complex as a catalyst. The compound of formula (I) which is useful for synthesizing a 4-acetoxyazetidin-2-one derivative, a useful intermediate for obtaining penem antibiotics, can be prepared economically.

3 Claims, No Drawings

PROCESS FOR PREPARING OPTICALLY ACTIVE 3-HYDROXYBUTANOIC ACID

FIELD OF THE INVENTION

This invention relates to a process for preparing an optically active 3-hydroxybutanoic acid represented by formula (I):

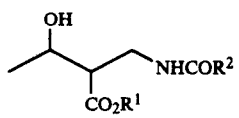

wherein:
$R^1$ represents a protective group for a carboxylic acid, and
$R^2$ represents a hydrogen atom; a lower alkyl group which may be substituted with a halogen atom; a lower alkoxy group; a phenyl group which may be substituted with a lower alkyl group or a lower alkoxy group; or a benzyloxy group which may be substituted with a lower alkyl group or a lower alkoxy group, which is useful as an intermediate for synthesizing penem antibiotics represented by thienamycin.

BACKGROUND OF THE INVENTION

Penem antibiotics represented by thienamycin have attracted attention as medicines because of their broad antimicrobial spectra:

Various processes for preparing penem antibiotics have been reported, e.g., in Kametani, *Heterocycles,* Vol. 17, pp. 463–506 (1982) and Shibuya, *Yuki Gosei Kaqaku Kwokai Shi* (Journal of Organic Synthetic Chemistry), Vol. 41, pp. 62 (1983). Among the proposed processes, a process using a 4-acetoxyzetidin-2-one derivative represented by formula (VII):

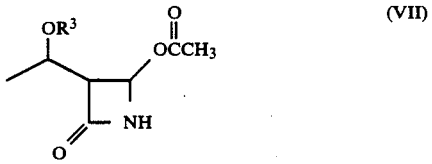

wherein $R^3$ represents a hydrogen atom or a protective group for a hydroxyl group, as an intermediate is advantageous for obtaining various kinds of penem antibiotics in that the compound of formula (VII) exhibits reactivity with various nucleophilic agents.

Known processes for preparing the 4-acetoxyazetidin-2one derivative of formula (VII) include those disclosed in *Tetrahedron Letters,* Vol. 23, pp. 2293 (1982); *Tetrahedron,* Vol. 39, pp. 2399 (1983); ibid, Vol. 39, pp. 2505 (1983); JP-A-59-181254; JP-A-61-50964; and JP-A-63-45251(the term "JP-A" as used herein means an "unexamined published Japanese patent application").

However, these known processes must start with expensive raw materials, and it has therefore been demanded to develop an economical process.

SUMMARY OF THE INVENTION

In the light of the above-described situation, the inventors have conducted extensive investigations. As a result, it has now been found that the 4-acetoxyazetidin-2-one derivative of formula (VII) can be prepared with advantages by using an optically active 3-hydroxybutanoic acid represented by formula (I) shown above. The inventors have also developed an advantageous process for preparing the optically active 3-hydroxybutanoic acid of formula (I). The present invention has been completed based on these findings.

That is, the present invention provides a process for preparing an optically active 3-hydroxybutanoic acid represented by formula (I), which comprises asymmetrically hydrogenating a 3-oxobutanoic acid ester represented by formula (II):

wherein $R^1$ and $R^2$ are as defined above, in the presence of a ruthenium-optically active phosphine complex as a catalyst.

DETAILED DESCRIPTION OF THE INVENTION

The starting compound of formula (II) which can be used in the process of this invention can be prepared easily from acetoacetic esters according to the process described in Ber., Vol. 92, pp. 1599 (1959).

Specific examples of the 3-oxobutanoic ester of formula (II) are methyl 2-(N-acetylamino)methyl-3-oxobutanoate, ethyl 2-(N-acetylamino)methyl-3-oxobutanoate, isopropyl 2-(N-acetylamino)methyl-3-oxobutanoate, butyl 2-(N-acetylamino)methyl-3-oxobutanoate, t-butyl 2-(N-acetylamino)methyl-3-oxobutanoate, phenyl 2-(N-acetylamino)methyl-3-oxobutanoate, benzyl 2-(N-acetylamine)methyl-3-oxobutanoate, methyl 2-(N-benzoylamino)methyl-3oxobutanoate, propyl 2-(N-benzoylamino)methyl-3-oxobutanoate, ethyl 2-(N-benzoylamino)methyl-3-oxobutanoate, p-methoxyphenyl 2-(N-benzoylamino)-methyl-3-oxobutanoate, p-methoxybenzyl 2-(N-benzoylamino)methyl-3-oxobutanoate, p-methylbenzyl 2-(N-benzoylamine)methyl-3-oxobutanoate, methyl 2-(N-formylamino)methyl-3-oxobutanoate, isopropyl 2-(N-formylamino)methyl-3-oxobutanoate, methyl 2-(N-carboethoxyamino)methyl-3-oxobutanoate, ethyl 2-(N-carboethoxyamino)methyl-3-oxobutanoate, ethyl 2-(N-carbobenzyloxyamino)methyl-3-oxobutanoate, methyl 2-(N-chloroacetylamino)methyl-3-oxobutanoate, ethyl2-(N-dichloroacetylamino)methyl-3-oxobutanoate, methyl 2-(N-trichloroacetylamino)methyl-3-oxobutanoate, ethyl 2-(N-pivaloylamino)methyl-3-oxobutanoate, and isopropyl 2-(N-propionylamino)-methyl-3-oxobutanoate.

The compound of formula (I) can be prepared from the compound of formula (II) by subjecting the compound of formula (II) to stereoselective hydrogenation using a ruthenium-optically active phosphine complex as a catalyst.

The ruthenium-optically active phosphine complex to be used includes:
(1) $Ru_xH_yCl_z(R\text{-BINAP})_2(Q)_p$
wherein R-BINAP represents a tertiary phosphine represented by the formula:

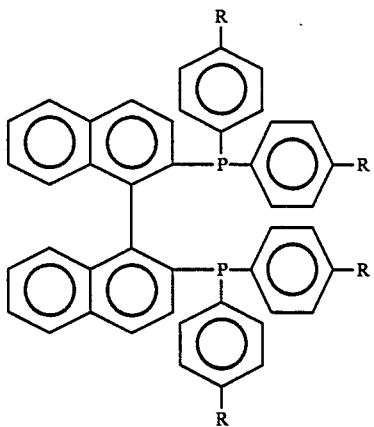

wherein R represents a hydrogen atom, a methyl group, or a t-butyl group; Q represents a tertiary amine; when y is 0, then x represents 2, z represents 4, and p represents 1; and when y is 1, then x represents 1, z represents 1, and p represents 0.

(2) [RuH$_u$(R-BINAP)$_v$]Y$_w$ wherein R-BINAP is as defined above; Y represents ClO$_4$, BF$_4$, or PF$_6$; when us is 0, then v represents 1, and w represents 2; and when u is 1, then v represents 2, and w represents 1.

(3) Ru(R-BINAP)

(OCR$^3$)$_2$ wherein R-BINAP is as defined above; and R$^3$ represents a lower alkyl group or a trifluoromethyl group.

(4) [Ru(R-BINAP)MCl$_k$]$_l$X$_m$ wherein R-BINAP is as defined above; M represents Zn, Al, Ti, or Sn; X represents N(C$_2$H$_5$)$_3$ or CH$_3$CO$_2$; when X is N(C$_2$H$_5$)$_3$, then l represents 2, m represents 1, and k represents 4 when M is Zn, 5 when M is Al, or 6 when M is Ti or Sn; and when X is CH$_3$CO$_2$, then l represents 1, m represents 2, and k represents 2 when M is Zn, 3 when M is Al, or 4 when M is Ti or Sn.

The ruthenium-optically active phosphine complex (1) can be obtained by the processes disclosed in T. Ikariya, et al., *J. Chem. Soc., Chem. Commun.*, pp. 922–924 (1985) and JP-A-61-63690.

The complexes (2) and (3) can be prepared by the processes disclosed in JP-A-63-41487 and JP-A-62-205266.

The complex (4) can be prepared using, for example, Ru$_2$Cl$_4$(R-BINAP)$_2$(NEt$_3$) (Et represents an ethyl group, hereinafter the same) or Ru(R-BINAP)(OCOCH$_3$)$_2$ as a starting material. In some detail, Ru$_2$Cl$_4$(R-BINAP)$_2$(NEt$_3$) is reacted with a Lewis acid selected from zinc chloride, aluminum chloride, titanium tetrachloride, and tin tetrachloride in a solvent, e.g., methylene chloride, at 10° to 25° C. for 2 to 20 hours, the solvent is removed by distillation, and the residue is dried to solid to a obtain the desired ruthenium-phosphine complex. Alternatively, Ru(R-BINAP)-(OCOCH$_3$)$_2$ and the above-described Lewis acid are reacted in a solvent, e.g., methylene chloride, at 10° to 25° C. for 2 to a 20 hours, the solvent is removed by distillation, and the residue is dried to solid to obtain the desired ruthenium-phosphine complex.

Specific examples of the ruthenium-optically active phosphine complex which can be used in the present invention are shown below:

Ru$_2$Cl$_4$(BINAP)$_2$(NEt$_3$)
    [wherein BINAP represents 2,2'-bis(diphenylphosphino)-1,1'-binaphthyl]
Ru$_2$Cl$_4$(T-BINAP)$_2$(NEt$_3$)
    [wherein T-BINAP represents 2,2'-bis(di-p-tolylphosphino)-1,1'-binaphthyl]
Ru$_2$Cl$_4$(t-Bu-BINAP)$_2$(NEt$_3$)
    [wherein t-Bu-BINAP represents 2,2,'-bis(di-p-t-butylphenylphosphine)-1,1'-binaphthyl]
RuHCl(BINAP)$_2$
RuHCl(T-BINAP)$_2$
RuHCl(t-Bu-BINAP)$_2$
[Ru(BINAP)](ClO$_4$)$_2$
[Ru(T-BINAP)](ClO$_4$)$_2$
[Ru(t-Bu-BINAP)](ClO$_4$)$_2$
[Ru(BINAP)](BF$_4$)$_2$
[Ru(T-BINAP)](BF$_4$)$_2$
[Ru(t-Bu-BINAP)](BF$_4$)$_2$
[Ru(BINAP)](PF$_6$)$_2$
[Ru(T-BINAP)](PF$_6$)$_2$
[RuH(BINAP)$_2$]ClO$_4$
[RuH(T-BINAP)$_2$]ClO$_4$
[RuH(BINAP)$_2$]BF$_4$
[RuH(T-BINAP)$_2$]BF$_4$
[RuH(BINAP)$_2$]PF$_6$
[RuH(T-BINAP)$_2$]PF$_6$
Ru(BINAP)(OCOCH$_3$)$_2$
Ru(BINAP)OCOCF$_3$)$_2$
Ru(T-BINAP)(OCOCH$_3$)$_2$
Ru(BINAP)(OCO-t-Bu)$_2$
    [wherein t-Bu represent t-butyl]
Ru(T-BINAP)(OCOCF$_3$)$_2$
Ru(t-Bu-BINAP)(OCOCH$_3$)$_2$
[Ru(BINAP)ZnCl$_4$]$_2$(NEt$_3$)
[Ru(BINAP)AlCl$_5$]$_2$(NEt$_3$)
[Ru(BINAP)SnCl$_6$]$_2$(NEt$_3$)
[Ru(BINAP)TiCl$_6$]$_2$(NEt$_3$)
[Ru(T-BINAP)ZnCl$_4$]$_2$(NEt$_3$)
[Ru(T-BINAP)AlCl$_5$]$_2$(NEt$_3$)
[Ru(T-BINAP)SnCl$_6$]$_2$(NEt$_3$)
[Ru(T-BINAP)TiCl$_6$]$_2$(NEt$_3$)
[Ru(BINAP)ZnCl$_2$](OCOCH$_3$)$_2$
[Ru(BINAP)AlCl$_3$](OCOCH$_3$)$_2$
[Ru(BINAP)SnCl$_4$](OCOCH$_3$)$_2$
[Ru(BINAP)TiCl$_4$](OCOCH$_3$)$_2$
[Ru(T-BINAP)ZnCl$_2$](OCOCH$_3$)$_2$
[Ru(T-BINAP)AlCl$_3$](OCOCH$_3$)$_2$
[Ru(T-BINAP)SnCl$_4$](OCOCH$_3$)$_2$
[Ru(T-BINAP)TiCl$_4$](OCOCH$_3$)$_2$ Hydrogenation of the compound of formula (II) is carried out in a halogenated hydrocarbon solvent (e.g., methylene chloride, dichloroethane, and trichloroethane) in the presence of the above-described ruthenium-optically active phosphine complex under a hydrogen pressure of from 10 to 150 kg/cm$^2$, preferably from 40 to 100 kg/cm$^2$, at a temperature of from 15° to 100° C., preferably from 35° to 70° C., for a period of from 10 to 40 hours, preferably from 15 to 30 hours. The amount of the ruthenium-optically active phosphine complex to be used ranges from 1/50 to 1/5000, preferably from 1/50 to 1/200, mole per mole of the compound of formula (II). The solvent is used in an amount of from 2 to 20 times, preferably from 4 to 7 times, the weight of the compound of formula (II).

In the reaction, the compound of formula (I) of a desired steric configuration can be obtained by selecting the BINAP moiety of the ruthenium-optically active phosphine complex. For example, use of an (R)-(+)-BINAP moiety results in the production of (2S, 3R)-compounds, and use of an (S)-(-)BINAP moiety results in the production of (2R, 3S)-compounds. In particular, the (2S, 3R)-compounds of formula (I) are useful for obtaining (1'R, 3R, 4R)-4-acetoxyazetidin-2-one derivatives, which are intermediates for synthesizing thienamycin.

The compound of formula (I) according to the present invention can be led to 4-acetoxyazetidin-2-one derivatives of formula (VII) according to the following reaction route:

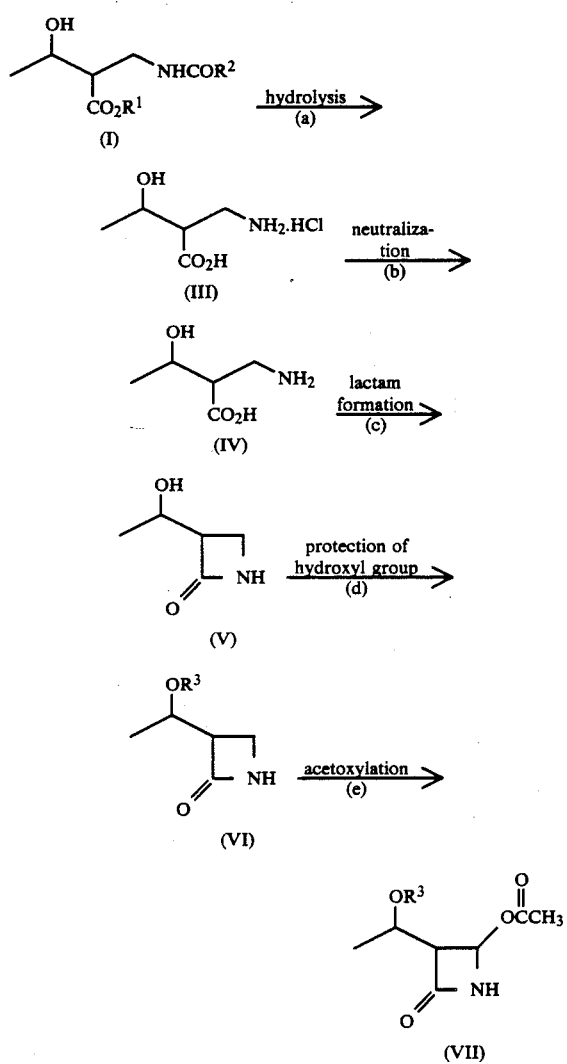

wherein $R^1$ and $R^2$ are as defined above; and $R^3$ represents a hydrogen atom or a protective group for a hydroxyl group.

That is, the compound of formula (I) is hydrolyzed with a dilute acid, etc., to form the compound of formula (III), which is then, if necessary, neutralized with an amine compound to obtain the compound of formula (IV). The compound of formula (IV) is cyclized with a lactam forming agent to obtain the lactam compound of formula (V). The compound of formula (V), if necessary, with its hydroxyl group protected to from the compound of formula (VI), is then acetoxylated with peracetic acid using a ruthenium compound as a catalyst to obtain the 4-acetoxyazetidin-2-one derivative of formula (VII).

In what follows, the reactions illustrated above are described in greater detail.

(a) Hydrolysis:

If desired, the compound of formula (I) is first purified by, for example, silica gel column chromatography. A 7/3 (by volume) mixed solvent of hexane and isopropyl alcohol is a preferred eluent. The compound is treated with a dilute acid, e.g., a 10 to 25% hydrochloric acid aqueous solution and a 5 to 30% sulfuric acid aqueous solution, at a temperature of from 30° to 110° C., preferably around 100° C., for a period of from 1 to 10 hours, preferably from 4 to 5 hours, to thereby hydrolyze the ester group and the acylamino group.

The amount of the dilute acid to be used is from an equivalence to 10 times, preferably 4 times, the volume of the substrate.

After the hydrolysis, the reaction mixture is cooled and washed with dichloromethane, ethyl acetate, toluene, etc., and the aqueous solution is concentrated to obtain the compound of formula (III).

(b) Neutralization:

The compound of formula (III) is dissolved in an adequate amount (3 to 20 times the volume) of a solvent, e.g., water, methanol, and ethanol, and neutralized with an equivalent amount of an alkali hydroxide, e.g., sodium hydroxide, followed by concentration to obtain a white solid which is a mixture of a free amino acid and a neutralized salt.

Alternatively, the compound of formula (III) is mixed with acetonitrile in an amount of from 10 to 30 times, preferably 20 times, the volume of the compound of formula (III) and a tertiary amine (e.g., triethylamine) in an equivalent amount to the compound of formula (III), and the mixture is stirred at room temperature for a period of from 10 to 30 hours to give the compound of formula (IV) (free amino acid) as a white crystal.

The process for obtaining the compound of formula (IV) is not limited to the above-described reaction route, and various known techniques for neutralization can be employed.

The thus obtained crude crystals are purified in a usual manner to obtain the compound of formula (IV).

(c) Lactam Formation:

To the amino acid salt of formula (III) obtained by the step (a) or the free amino acid of formula (IV) obtained through the steps (a) and (b) are added an equimolar amount of triphenylphosphine and an equimolar amount of dipyridyl disulfide, and triethylamine and acetonitrile are further added thereto.

The amount of triethylamine to be added is preferably 2 mole per mole of the compound of formula (III) or 1 mole per mole of the compound of formula (IV). The amount of acetonitrile to be used preferably ranges from 10 to 200 times, more preferably from 80 to 150 times, the volume of the compound of formula (III) or (IV).

The mixture is stirred at a temperature of from 25° to 85° C., preferably around 80° C., for a period of from 1 to 30 hours, preferably about 15 hours.

After completion of the reaction, the solvent is removed by distillation under reduced pressure of from 15 to 30 mmHg, and the residual oil is purified in a usual manner to obtain the lactam compound of formula (V).

The cyclization technique is not limited to the above-described process. For example, the process disclosed in Sunggak Kim et al., *Synthetic Communications*, Vol. 18, pp. 247 (1988) is also suitable to obtain the compound of formula (V).

(d) Protection of Hydroxyl Group:

If desired, the hydroxyl group of the compound of formula (V) may be protected using a commonly employed protecting agent in accordance with a known process.

Examples of suitable protective groups include those generally employed as a protective group for a hydroxyl group of lactam compounds, e.g., t-butyldimethylsilyl, triisopropylsilyl, acetyl, chloroacetyl, dichloroacetyl, trichloroacetyl, benzyloxycarbonyl, o-nitrobenzyloxycarbonyl, p-nitrobenzyloxycarbonyl, t-butyl, benzyl, 2,4-dimethoxybenzyl, trichloroethoxycarbonyl, and t-butoxycarbonyl groups.

(e) Acetoxylation:

To the compound of formula (V) or (VI), preferably the latter compound, is added a ruthenium compound as a catalyst in an amount of from 1/5 to 1/500 mole per mole of the substrate, i.e., the compound of formula (V) or (VI), using methylene chloride, acetic acid, acetonitrile, etc., as a solvent. An acetic acid or acetone solution containing peracetic acid in an amount of from 1 to 2 mole per mole of the substrate is then added dropwise to the solution at −30° C. to 30° C., preferably −5° C. to 0° C.

The ruthenium compound which can be used includes a ruthenium halide or a complex compound thereof, a ruthenium salt, and ruthenium-on-carrier. Examples of suitable ruthenium compounds are $RuCl_3$, $RuBr_3$, $RuI_3$, $RuCl_2(PPh_3)_3$ (PPh$_3$ represents triphenylphosphine, hereinafter the same), $HRuCl(PPh_3)_3$, $H_2Ru(PPh_3)_4$, $[Ru(NH_3)_5Cl]Cl_2$, $Ru(NH_3)_6Cl_3$, $Ru(NO)(NO_3)_3$,

Ru-acetylacetonate, $Ru_2Cl_4(BINAP)_2NEt_3$, $Ru_2Cl_4(1,4$-diphos$)_2$, $Ru(NO)Cl_3 \cdot H_2O$, $[Ru(NH_3)_5Br]Br_2$, $HRuCl(BINAP)_2$, $Ru(NH_3)_6I_3$, Ru-on-carbon, Ru-on-alumina, Ru-on-silica gel, Ru-on-silica-alumina, Ru-on-zirconia, Ru-on-diatomaceous earth, Ru-on-graphite, and Ru-on-iron oxide. In the case of the Ru-on-carrier catalysts, the amount of ruthenium supported is from 1 to 20% by weight, preferably 5% by weight, based on the carrier.

After the dropwise addition, the mixture is stirred for 0.5 to 5 hours, preferably 1 to 2 hours, to complete the reaction. After completion of the reaction, the solvent is removed by distillation, and the residue is purified in a usual manner to obtain the 4-acetoxyazetidin-2-one derivative of formula (VII).

If desired, the acetoxylation reaction may be carried out in the presence of sodium acetate in an amount of from 1 to 2 mole per mole of the substrate, thereby increasing the yield.

The thus obtained 4-acetoxyazetidin-2-one derivative of formula (VII) is useful as an intermediate for syntheses of penem antibiotics as disclosed in JP-A-58-103358.

According to the process of this invention, the compound of formula (I) which is useful for synthesis of the compound of formula (VII), a useful intermediate for penem antibiotics, can be prepared economically.

The present invention is now illustrated in greater detail by way of the following Examples and Reference Examples, but it should be understood that the present invention is not construed as being limited thereto. In these examples, all the parts and percents are by weight unless otherwise indicated. In Reference Examples, $^{31}P$ nuclear magnetic resonance spectra ($^{31}P$-NMR) were determined using Model AM 400 (161 MHz) manufactured by Bruker Inc., and the chemical shifts were measured using 85% phosphoric acid as an external standard.

REFERENCE EXAMPLE 1

Synthesis of $Ru_2Cl_4((+)$-BINAP$)_2(NEt_3)$ (di[2,2,'-bis(dipehnylphosphino)-1,1'-binaphthyl]tetrachloro-diruthenium triethylamine)

To 100 ml of toluene were added 1 g (3.56 mmole) of $[RuCl_2(COD)]_n$, 2.66 g (4.27 mmole) of (+)-BINAP, and 1.5 g of triethylamine in a nitrogen atmosphere. The mixture was heated at reflux for 10 hours, and the solvent was removed by distillation under reduced pressure. The precipitated crystals were dissolved in methylene chloride, and the solution was filtered through Celite. The filtrate was concentrated to dryness to give 3.7 g of $[Ru_2Cl_4((+)$-BINAP$)_2(NEt_3)]$ as a deep brown solid.

Elemental Analysis for $C_{94}H_{79}Cl_4NP_4Ru_2$:

Calcd. (%): Ru: 1196; C 66.85; H 4.71; P 7.33.

Found (%): Ru: 11.68; C 67.62; H 4.97; P 6.94.

$^1$H-NMR (CDCl$_3$) δ ppm: 1.30–1.50 (t, 6H, NCH$_2$CH$_3$), 3.05–3.30 (q, 4H, NCH$_2$CH$_3$), 6.40–8.60 (m, 32H, Ar-H)

REFERENCE EXAMPLE 2

Synthesis of [Ru((-)-T-BINAP)](ClO$_4$)$_2$([2,2,'-bis(di-p-tolylphosphino)-1,1'-binaphthyl]ruthenium perchlorate)

In a 250 ml-volume Schlenk's tube was put 0.54 g (0.30 mmole) of Ru$_2$Cl$_4$((-)-T-BINAP)$_2$(NEt$_3$). After thoroughly displacing the atmosphere with nitrogen, 60 ml of methylene chloride was added thereto. Subsequently, a solution of 0.73 g (6.0 mmole) of sodium perchlorate in 60 ml of water and a solution of 16 mg (0.06 mmole) of triethylbenzylammonium bromide in 3 ml of water were added thereto, followed by stirring at room temperature for 12 hours to conduct a reaction. After completion of the reaction, the reaction mixture was allowed to stand, and the aqueous layer was removed by liquid-liquid separation. The methylene chloride was removed by distillation under reduced pressure, and the residue was dried under reduced pressure to obtain 0.59 g (yield: 99.6%) of [Ru((-)-T-BINAP)](ClO$_4$)$_2$ as a deep brown solid.

Elemental Analysis for $C_{48}H_{40}Cl_2O_8P_2Ru$:

Calcd. (%): Ru 10.32; P 6.33; C 58.90; H 4.12.

Found (%): Ru 10.08; P 5.97; C 58.61; H 4.53.

$^{31}$P-NMR (CDCl$_3$) δ ppm: 12.920 (d, J=41.1 Hz), 61.402 (d, J=41.1 Hz)

REFERENCE EXAMPLE 3

Synthesis of Ru((−−-BINAP)(OCOCH₃)₂
([2,2′,-bis(diphenylphosphino)-1,1′-binaphthyl]ruthenium-diacetate)

In a 250 ml-volume Schlenk's tube were charged 1.43 g (0.85 mmole) of Ru₂Cl₄((-)-BINAP)₂(NEt₃) complex and 3.06 g (37 mmole) of sodium acetate. After thoroughly displacing the atmosphere with nitrogen, 100 ml of t-butanol was added thereto, followed by heating at reflux for 12 hours. After completion of the reaction, the t-butanol was removed from the reaction mixture by distillation under reduced pressure of 20 mmHg, and the residual solid was extracted twice with 10 ml portions of diethyl ether. The diethyl ether was removed by distillation, and the resulting solid was further extracted twice with 10 ml portions of ethanol, and the extract was concentrated to dryness to obtain 1.50 g of crude Ru((-)-BINAP)(OCOCH₃)₂. Recrystallization of the crude product from ethyl acetate gave 0.79 g (yield: 52%) of a yellowish brown solid.

Melting Point: 180°–181° C. (with decomposition
Elemental Analysis for $C_{48}H_{38}O_4P_2Ru$:
Calcd. (%): Ru 12.01; P 7.36; C 68.48; H 4.55
Found (%): Ru 11.85; P 7.28; C 68.35; H 4.61
$^{31}P\text{-}NMR$ (CDCl₃) δ ppm: 65.00 (s)
¹H-NMR (CDCl₃) δ ppm: 1.75 (s, 6H,

OCCH₃), 6.5–7.8 (m, 32H, naphthyl ring and phenyl proton)

REFERENCE EXAMPLE 4

Synthesis of [Ru((-)-T-BINAP)SnCl₆]₂(NEt₃)
(bis,[ruthenium(2,2,′-bis(di-p-tolylphosphino)-1,1′-binaphthyl)hexachlorotin]triethylamine In a 80 ml-volume Schlenk's tube was charged 0.52 g (0.3 mmole) of Ru₂Cl₄((-)-T-BINAP)₂(NEt₃). After thoroughly displacing the atmosphere with nitrogen, 20 ml of methylene chloride and 0.16 g (0.6 mmole) of SnCl₄ were added thereto, followed by stirring at room temperature for 15 hours. After completion of the reaction, the methylene chloride was removed to dryness by distillation under reduced pressure to obtain 0.68 g (yield: 100%) of [Ru((-)-T-BINAP)SnCl₆]₂(NEt₃) as a deep brown solid.

Elemental Analysis for $C_{102}H_{95}Cl_{12}NP_4Sn_2Ru_2$:
Calcd. (%): P 5.91; C 53.48; H 4.36; Cl 17.56.
Found (%) P 5.33; C 52.72; H 4.12; Cl 18.31.
$^{31}P\text{-}NMR$ (CDCl₃) δ ppm: 14.14 (d, J=41.7 Hz), 62.57 (d, J=41.7 Hz)

EXAMPLE 1

In a 100 ml-volume stainless steel-made autoclave whose atmosphere had been displaced with nitrogen was charged a solution of 2.5 g (10 mmole) of methyl 2-(N-benzoylamino)methyl-3-oxobutanoate and 84.5 mg (0.05 mmole) of the ruthenium-optically active phosphine complex as synthesized in Reference Example 1 [Ru₂Cl₄((+)-BINAP)₂(NEt₃)] in 17.5 ml of methylene chloride, and the mixture was stirred at 50° C. under a hydrogen pressure of 100 kg/cm² for 20 hours to conduct a hydrogenation reaction. The solvent was removed from the reaction mixture by distillation, and the residue was purified by silica gel column chromatography using a mixed solvent of n-hexane and ethyl acetate as an eluent to obtain 2.25 g (yield: 90%) of methyl (2S, 3R)-2-(N-benzoylamino)methyl-3-hydroxybutanoate having an optical purity of 98 %ee.

The optical purity was determined on the (+)-methoxytrifluoromethyl-phenylacetic acid ester of the product by high performance liquid chromatography (HPLC) under the following conditions:

Column: Develosil 100-3 (4.6 mm×250 mm), produced by Nomura Kagaku K.K.
Determination UV Wavelength: 254 nm
Developing Solvent: Hexane/diethyl ether=90/10 by volume; flow rate=1 ml/min
$^{31}H\text{-}NMR$ (CDCl₃) δ ppm: 1.26 (d, J=6.25 Hz, 3H), 2.62 (m, 1H), 3.57–3.62 (m, 1H), 3.73 (s, 3H), 4.60–4.03 (m, 1H), 4.07–4.14 (m, 1H), 7.02 (br., s, 1H), 7.41–7.80 (m, 5H)

EXAMPLE 2

In a 100 ml-volume stainless steel autoclave whose atmosphere had been displaced with nitrogen was added a solution of 2.01 g (10 mmole) of ethyl 2-(N-acetylamino)methyl-3-oxobutanoate and 84.5 mg (0.05 mmole) of Ru₂Cl₄((+)-BINAP)₂NEt₃ in 18 ml of methylene chloride, and a reaction was conducted at 35° C. under a hydrogen pressure of 70 kg/cm² for 17 hours. The reaction mixture was taken out, concentrated under reduced pressure of 20 mmHg, and purified by silica gel column chromatography using a 7/3 (by volume) mixed solvent of hexane and isopropanol as an eluent to obtain 1.95 g (yield: 96.5%) of ethyl (2S, 3R)-2-(N-acetylamino)methyl-3-hydroxybutanoate having an optical purity of 98 %ee. The optical purity of the product was determined by HPLC in the same manner as in Example 1, except for using A-002-3 S-3 120A produced by Yamamura Kagaku Kenkyusho K.K. as a column and a 800/200/1 (by volume) mixture of hexane, tetrahydrofuran and methanol as an eluent.

$^{31}H\text{-}NMR$ (CDCl₃) δ ppm: 1.25 (d, J=6.3 Hz, 3H), 1.29 (t, J=7.1 Hz, 3H), 2.01 (s, 3H), 2.45–2.49 (m, 1H), 3.32–3.38 (m, 1H), 3.87–3.95 (m, 3H), 4.13–4.21 (m, 2H), (br., s, 1H)

EXAMPLE 3

In a 100 ml-volume stainless steel autoclave whose atmosphere had been displaced with nitrogen was added a solution of 2.31 g (10 mmole) of ethyl 2-(N-carboethoxyamino)methyl-3-oxobutanoate and 84.5 mg (0.05 mmole) of Ru₂Cl₄((+)-BINAP)₂NEt₃ in 18 ml of methylene chloride, and a reaction was conducted at 45° C. under a hydrogen pressure of 75 kg/cm² for 20 hours. The reaction mixture was taken out and concentrated under reduced pressure of 20 mmHg. The concentrate was purified by silica gel chromatography using a 8/2 (by volume) mixture of hexane and isopropanol as an eluent to obtain 1.63 g (yield: 70%) of ethyl (2S, 3R)-2-(N-carboethoxyamino)methyl-3-hydroxybutanoate having an optical purity of 90 %ee as determined in the same manner as in Example 2, except for using a 1000:100:1 (by volume) mixture of hexane, tetrahydrofuran and methanol as an eluent.

¹H-NMR (CDCl₃) δ ppm: 1.21–1.30 (m, 9H), 2.50–2.53 (m, 1H), 3.41–3.50 (m, 1H), 3.60–3.72 (m, 1H), 4.05 (br., s, 1H), 4.08–4.25 (m, 4H), 5.37 (br., s, 1H)

EXAMPLE 4

In a 100 ml-volume stainless steel autoclave whose atmosphere had been displaced with nitrogen was added a solution of 2.21 g (10 mmole) of methyl 2-(N-chloroacetylamino)methyl-3-oxobutanoate and 180 mg (0.1 mmol) of Ru$_2$Cl$_4$((+)-T-BINAP)$_2$NEt$_3$ in 20 ml of methylene chloride, and a reaction was conducted at 50° C. under a hydrogen pressure of 100 kg/cm$^2$ for 20 hours. The reaction mixture was concentrated under reduced pressure of 20 mmHg and purified by silica gel chromatography using a 8/2 (by volume) mixture of hexane and isopropanol as an eluent to obtain 1.78 g (yield: 80%) of methyl (2S, 3R)-2-(N-chloroacetylamino)methyl-3-hydroxybutanoate having an optical purity of 95 %ee as determined in the same manner as in Example 2.

$^1$H-NMR (CDCl$_3$) δ ppm: 1.24 (d, J=6.3 Hz, 3H), 1.28 (t, J=7.1 Hz, 3H), 2.47–2.52 (m, 1H), 3.35–3.40 (m, 1H), 3.90–3.98 (m, 3H), 4.05 (s, 2H), 4.15–4.24 (m, 2H), 6.75 (br., s, 1H)

EXAMPLE 5

In 100 ml-volume stainless steel autoclave whose atmosphere had been displaced with nitrogen was added a solution of 2.01 g (10 mmole) of ethyl 2-(N-acetylamino)methyl-3-oxobutanoate and 168 mg (0.1 mmole) of

((+)-BINAP) in 15 ml of methylene chloride, and a reaction was conducted at 70 ° C. under a hydrogen pressure of 130 kg/cm$^2$ for 30 hours. The reaction mixture was concentrated, and the residue was purified by silica gel chromatography using a 7/3 (by volume) mixture of hexane and isopropanol as an eluent to give 1.7 g (yield: 85%) of ethyl (2S, 3R)-2-(N-acetylamino)-methyl-3-hydroxybutanoate having an optical purity of 93 %ee as determined in the same manner as in Example 2.

EXAMPLE 6

In a 100 ml-volume stainless steel autoclave whose atmosphere had been displaced with nitrogen was added a solution of 2.5 g (10 mmole) of methyl 2-(N-benzoylamino)methyl-3-oxobutanoate and 184 mg (0.1 mmole) of [Ru((+)BINAP)](ClO$_4$)$_2$ in 18 ml of dichloroethane, and a reaction was conducted at 70° C. under a hydrogen pressure of 100 kg/cm$^2$ for 30 hours. The reaction mixture was concentrated under reduced pressure of 20 mmHg, and the residue was purified by silica gel column chromatography using a 7/3 (by volume) mixture of hexane and isopropanol as an eluent to give 2.19 g (yield: 86.5%) of methyl (2S, 3R)-2-(N-benzoylamino)methyl-3-hydroxybutanoate having an optical purity of 90 %ee.

EXAMPLE 7

The same procedure of Example 1 was repeated, except for using 245 mg (0.2 mmole) of [Ru((+)-BINAP)SnCl$_6$]$_2$(NEt$_3$) as a catalyst to obtain methyl (2S, 3R)-2-(N-benzoylamino)methyl-3-hydroxybutanoate having an optical purity of 93 %ee in a yield of 85%.

EXAMPLE 8

In a 100 ml-volume autoclave whose atmosphere had been displaced with nitrogen was added a methylene chloride solution of 2.5 g of methyl 2-(N-benzoylamino)methyl-3-oxobutanoate and 84.5 mg (0.05 mmole) of Ru$_2$Cl$_4$((-)-BINAP$_2$(NEt$_3$), and a reaction was conducted by stirring at 45° C. under a hydrogen pressure of 70 kg/cm$^2$ for 24 hours. The reaction mixture was taken out, and the solvent was removed by distillation under reduced pressure of 20 mmHg at 30° C. The residue was purified by silica gel column chromatography using a 7/3 (by volume) mixture of hexane and isopropanol as an eluent to obtain 2.27 g (yield: 91%) of methyl (2R, 3S)-2-(N-benzoylamino)methyl-3-hydroxybutanoate having an optical purity of 97 %ee.

REFERENCE EXAMPLE 5

To 10.65 g (42.43 mmole) of methyl (2S, 3R)-2-(N-benzoylamino)methyl-3-hydroxybutanoate was added 70 ml of a 10% hydrochloric acid aqueous solution at room temperature to form a solution. The solution was heated at reflux for 4.5 hours and then allowed to cool to room temperature. The precipitated benzoic acid was separated by filtration, and the filtrate was washed twice with 100 ml portions of toluene. The aqueous layer was concentrated under reduced pressure to obtain 6.67 g (yield: 93%) of (2S, 3R)-2-aminomethyl-3-hydroxybutanoic acid hydrochloride.

$^1$H-NMR (CD$_3$OD) δ ppm: 1.32 (3H, d, J=6.54), 2.85 (1H, m), 3.37 (2H, m), 4.33 (1H, dq, J=6.54, 4.99)

REFERENCE EXAMPLE 6

To 6.14 g (36.22 mmole) of (2S, 3R)-2-aminomethyl-3-hydroxybutanoic acid hydrochloride was added 150 ml of acetonitrile, and 5.05 ml (36.22 mmole) of triethylamine was further added thereto under ice-cooling, followed by vigorously stirring at room temperature for 2 days. The precipitated powderous crystals were collected by filtration, washed with of acetonitrile, and filtered to recover 4.07 g (yield: of crystals of (2S, 3R)-2-aminomethyl-3-hydroxybutanoic acid.

$^1$H-NMR (CD$_3$OD) δ ppm: 1.27 (3H, d, J=6.39), 2.49 (1H, dt, J=6.21, 6.36), 3.26 (2H, d, J=6.36), 4.10 (1H, dq, J=6.21, 6.39)

REFERENCE EXAMPLE 7

In 2.28 g (17.14 mmole) of (2S, 3R)-2-aminomethyl-3-hydroxybutanoic acid was suspended 342 ml of anhydrous acetonitrile, and 5.49 g (20.93 mmole) of triphenylphosphine and 4.54 g (20.61 mmole) of dipyridyl disulfide were added thereto. A reaction was conducted at 55° to 60° C. for 20 hours. The reaction mixture was concentrated under reduced pressure, and the residue was purified by silica gel column chromatography using an 8/8/1 (by volume) mixture of methylene chloride, ethyl acetate, and methanol as an eluent to obtain 1.64 g (yield: 83%) of (1'R, 3S)-3'-(1,-hydroxy)ethylazetidin-2-one.

$^1$H-NMR (CDCl$_3$) δ ppm: 1.28 (3H, d, J=6.3), 2.10 (1H, -OH), 3.31 (1H, ddd, J=5.4, 5.3, 2.7), 3.36 (2H, ddd, J=5.2, 5.2, 2.7), 4.21 (1H, dq, J=6.3, 5.4), 5.82 (1H, -NH)

REFERENCE EXAMPLE 8

In 15 ml of anhydrous dimethylformamide was dissolved 3.88 g (33.74 mmole) of (1'R, 3S)-3-(1,'-hydroxy)ethylazetidin-2one, and 2.41 g (35.43 mmole) of imidazole and 5.34 g (35.43 mmole) of t-butyldimethylsilyl chloride were added to the solution, and a reaction was conducted at room temperature for 20 hours. The reaction mixture was poured into 100 ml of cold water, and the precipitated crystals were collected by filtration to obtain 6.5 g (yield: 84%) of (1'R, 3S)-3-(1'-t-butyldimethylsilyloxy)ethylazetidin-2-one having an optical purity of 94 %ee.

Melting Point: 66°-68° C.
$[\alpha]_D^{25} -69.8°$ (c=1.02; CHCl$_3$)
$^1$H-NMR (CDCl$_3$) δ ppm: 0.09 (6H, s), 0.88 (9H, s), 1.21 (3H, d, J=6.21), 3.21 (1H, m), 3.30 (1H, dd, J=5.08, 5.26), 3.37 (1H, m), 4.20 (1H, dq, J=5.26, 6.21), 5.63 (1H, -NH)

REFERENCE EXAMPLE 9

In 20 ml of anhydrous acetonitrile was dissolved 0.50 g (2.18 mmole) of (1'R, 3S)-3-(1'-t-butyldimethylsilyloxy)ethyl-azetidin-2-one in a nitrogen stream, and 0.18 g (2.18 mmole) of sodium acetate was added thereto. To the solution was added 20 ml of an anhydrous acetonitrile solution containing 45 mg (0.22 mmole) of ruthenium trichloride, followed by cooling to −5° C. Further, 3 ml of a 40% peracetic acid solution was carefully added dropwise to the solution. The solvent was removed by distillation under reduced pressure, and the residue was purified by silica gel column chromatography to obtain 0.5 g (yield: 80%) of (1'R, 3R, 4R)-4-acetoxy-3-(1'-t-butyl-dimethylsilyloxy)ethylazetidin-2-one having an optical purity of 99.2 %ee.
$[\alpha]_D^{25} +47.8°$ (c=0.98, CHCl$_3$)
$^1$H-NMR (CDCl$_3$) δ ppm: 0.08 (3H, s), 0.09 (3H, s), 0.88 (9H, s), 1.27 (3H, d, J=6.35), 2.11 (3H, s), 3.19 (1H, dd, J=3.50, 1.27), 4.23 (1H, dq, J=3.50, 6.35), 5.84 (1H, d, J=1.27), 6.40 (1H, -NH)

REFERENCE EXAMPLES 10 to 20

The same procedure of Reference Example 9 was repeated, except for altering the catalyst and reaction conditions as shown in Table 1 below. The results obtained are also shown in Table 1.

TABLE 1

| Reference Example No. | Catalyst | Solvent | Substrate/Catalyst Molar Ratio | Yield (%) |
|---|---|---|---|---|
| 10 | RuCl$_2$(PPh$_3$)$_3$ | benzene | 50 | 12 |
| 11 | RuH$_2$(PPh$_3$)$_3$ | CH$_2$Cl$_2$ | 20 | 25 |
| 12 | Ru(OAc)$_2$(T-BINAP)* | " | 20 | 38 |
| 13 | Ru(acac)$_3$** | " | 20 | 58 |
| 14 | RuCl$_3$.3H$_2$O | " | 10 | 85 |
| 15 | RuBr$_3$ | " | 10 | 77 |
| 16 | RuI$_3$ | " | 10 | 75 |
| 17 | Ru(NH$_3$)$_6$Cl$_3$ | " | 10 | 55 |
| 18 | Ru(NO)Cl$_3$.H$_2$O | " | 10 | 70 |
| 19 | Ru-on-carbon | " | (3)*** | 80 |
| 20 | Ru-on-graphite | " | (3)*** | 72 |

Note:
*OAc represents acetoxy.
**Ru(acac)$_3$ represents ruthenium acetylacetonate
***Ratios in the parentheses are by weight.

While the invention has been described in detail and with reference to specific embodiments thereof, it will be apparent to one skilled in the art that various changes and modifications can be made therein without departing from the spirit and scope thereof.

What is claimed is:
1. A process for preparing an optically active 3-hydroxybutanoic acid represented by formula (I):

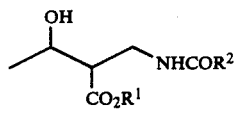    (I)

wherein:
R$^1$ represents a protective group for a carboxylic acid, and
R$^2$ represents a hydrogen atom; a lower alkyl group which may be substituted with a halogen atom; a lower alkoxy group; a phenyl group which may be substituted with a lower alkyl group or a lower alkoxy group; or a benzyloxy group which may be substituted with a lower alkyl group or a lower alkoxy group,
which comprises asymmetrically hydrogenating a 3-oxobutanoic acid ester represented by formula (II):

    (II)

wherein R$^1$ and R$^2$ are as defined above, in the presence of a ruthenium-optically active phosphine complex as a catalyst.

2. A process as claimed in claim 1, wherein said ruthenium-optically active phosphene complex is selected from the group consisting of:

(1) Ru$_x$H$_y$Cl$_z$(R-BINAP)$_2$(Q)$_p$
   wherein R-BINAP represents a tertiary phosphine represented by formula:

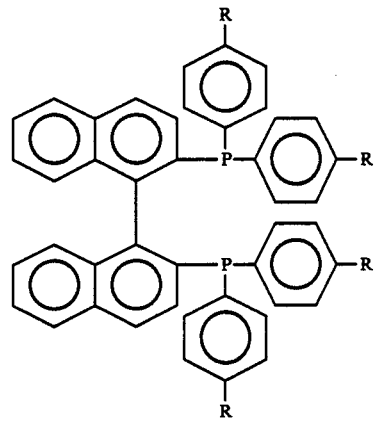

wherein R represents a hydrogen atom, a methyl group, or a t-butyl group; Q represents a tertiary amine; when y is 0, then x represents 2, z represents 4, and p represents 1; and when y is 1, then x represents 1, z represents 1, and p represents 0, (2) [RuH$_u$(R-BINAP)$_v$]Y$_w$
   wherein R-BINAP is as defined above; Y represents ClO$_4$, BF$_4$, or PF$_6$; when u is 0, then v represents 1, and w represents 2; and when u is 1, then v represents 2, and w represents 1, (3) Ru(R-BINAP)

(OCR$^3$)$_2$ wherein R-BINAP is as defined above; and R$^3$ represents a lower alkyl group or a trifluoromethyl group,
and
(4) [Ru(R-BINAP)MCl$_k$]$_l$X$_m$ wherein R-BINAP is as defined above; M represents Zn, Al, Ti, or Sn; X represents $N(C_2H_5)_3$ or $CH_3CO_2$; when X is $N(C_2H_5)_3$, then represents 2, m represents 1, and k represents 4 when M is Zn, 5 when M is Al, or 6 when M is Ti or Sn; and when X is $CH_3CO_2$, then l represents 1, m represents 2, and k represents 2 when M is Zn, 3 when M is Al, or 4 when M is Ti or Sn.

3. A process as claimed in claim 1, wherein said ruthenium-optically active phosphine complex is present in an amount of from 1/50 to 1/5000 mole per mole of the compound of formula (II).

* * * * *